United States Patent [19]

Takemura et al.

[11] Patent Number: 4,758,283
[45] Date of Patent: Jul. 19, 1988

[54] PROCESS FOR PREPARING L-RHAMNOSE

[75] Inventors: Motohiro Takemura, Kitamoto; Mochihiro Iljima, Kuki; Yoshiaki Tateno, Omiya; Naoki Okamoto; Masaaki Fuse, both of Tokyo, all of Japan

[73] Assignee: Towa Chemical Industry Co. Ltd., Japan

[21] Appl. No.: 945,073

[22] Filed: Dec. 22, 1986

[51] Int. Cl.$^4$ ............ C13K 1/00; C13D 1/00; C13D 1/14; C13J 1/06

[52] U.S. Cl. ................ 127/36; 127/43; 127/44; 127/46.1; 127/34; 127/53; 127/55; 127/56; 127/58; 536/128

[58] Field of Search ........... 127/44, 46.1, 46.2, 127/46.3, 36, 34, 43, 37, 53, 55, 56, 58; 536/128

[56] References Cited

U.S. PATENT DOCUMENTS 3,240,755  3/1966  Schweiger .................. 528/196
3,856,569  12/1974  Strong ....................... 127/34

FOREIGN PATENT DOCUMENTS 59268873  7/1986  Japan .

OTHER PUBLICATIONS

W. Pigman et al., The Carbohydrates, vol. IIB, 2nd ed., 1970, pp. 561–563.
Chemical Abstracts, vol. 90, 1979, p. 274, Abstract No. 100140x.
Chemical Abstracts, vol. 51, No. 4, 1957, Abstract No. 2955i.
Chemical Abstracts, vol. 95, 1981, p. 320, Abstract No. 192055c.

Primary Examiner—Helen M. S. Sneed
Assistant Examiner—Chung K. Pak
Attorney, Agent, or Firm—McGlew and Tuttle

[57] ABSTRACT

This invention relates to a process for readily and efficiently preparing L-rhamnose with the use of a marine alga belonging to the family Monostromaceae, Ulvales.

According to the process of the present invention, rhamnan sulfate is extracted from a marine alga belonging to the family Monostromaceae such as *Monostroma nitidium* Wittrock and the obtained extract is hydrolyzed by adding acid(s) thereto followed by heating or treating thereof with a cation exchange resin followed by heating to thereby give a solution containing free L-rhamnose.

Since the solution thus obtained contains a large amount of salts, the removal of these salts is significantly important in the preparation of L-rhamnose. In the present invention, an effective process therefor is combined with a conventional method by using an ion exchange resin to thereby establish an efficient desalting process.

Further it is effective to elevate the purity of L-rhamnose by adding baker's yeast, which selectively ferments various sugars, to the solution containing L-rhamnose.

18 Claims, No Drawings

PROCESS FOR PREPARING L-RHAMNOSE

TECHNICAL FIELD

This invention relates to a process for preparing L-rhamnose. More particularly, it relates to a process for efficiently preparing L-rhamnose by a simple procedure with the use of marine algae belonging to the family Monostromaceae, Ulvales, as a raw material.

BACKGROUND ART

L-Rhamnose, which is a typical 6-deoxyhexose similar to fucose and has a $CH_3$ group, is also called 6-deoxy-L-mannose, L-mannomethylose or isodulcitol. L-Rhamnose is usually obtained in the form of $\alpha$-type monohydrate crystal from its aqueous solution. This crystal has a melting point of 88° to 92° C. and is sublimable. The specific rotation of an aqueous solution thereof is initially levorotatory ($[\alpha]_D^{20} = -7.7°$) but it undergoes mutarotation to become dextrorotatory ($[\alpha]_D^{20} = $ ca. $+9°$) within approximately one hour.

L-Rhamnose exhibits a sweet and slightly bitter taste similar to that of D-mannose.

Recently it has been found that sugar chains comprising various monosaccharides have physiological activities. Thus there have been attempts to utilize these sugar chains as materials for pharmaceuticals and agricultural chemicals. L-Rhamnose or its derivatives are sometimes employed as the constituents of these sugar chains. Further it would be expected that L-rhamnose is available in the field of biotechnology including plant cytology, microbial technology, genetic engineering, fermentation technology and immunology. L-Rhamnose would be furthermore expected to be available as a material for a reaction flavor since it would undergo the Maillard reaction with an amino acid to thereby generate a characteristic smell.

L-Rhamnose widely occurs in nature, mainly in plants, as a constituent of glycosides such as rutin, xanthorhamnin, hesperidin or quercitrin, or a constituting sugar of, for example, gum arabic or karaya gum.

L-Rhamnose has been prepared by hydrolyzing the above-mentioned glycosides. However these glycosides are expensive and produced only in a limited amount, which makes the use thereof as the starting materials for the preparation of L-rhamnose difficult. In addition, the use of, for example, rutin is sometimes undesirable since it might be contaminated with quercetin which might be carcinogenic.

Japanese Patent Laid-Open No. 146200/1986 discloses a process for preparing L-rhamnose from gum arabic. This process requires use of a large amount of organic solvent(s) for the removal of impurities and for the separation of the aimed L-rhamnose from L-arabinose which is contained in the reaction mixture in the same amount as that of the L-rhamnose. Further an industrial chromatographic separation in this process requires a troublesome procedure as well as well-controlled equipment. Thus it is difficult to economically prepare L-rhamnose thereby.

As described above, it is very difficult at present to economically and stably supply L-rhamnose on an industrial scale. That is to say, when an expensive material produced in a limited amount, e.g., rutin is employed, the L-rhamnose thus obtained is also expensive. On the other hand, when gum arabic is employed as a material, the resulting sugar hydrolyzate has an undesirable composition, which makes it necessary to employ special equipment for, e.g., chromatographic separation to obtain L-rhamnose of a high purity.

DISCLOSURE OF THE INVENTION

Under these circumstances, we have attempted to solve these problems accompanying the conventional preparation of L-rhamnose to thereby economically provide L-rhamnose of excellent properties. As a result, we have found that marine algae belonging to the family monostromaceae, Ulvales, are extremely suitable as raw materials for the preparation of L-rhamnose and that L-rhamnose of excellent properties can be readily and efficiently prepared from these algae, thus completing the present invention.

Accordingly, the present invention provides a process for preparing L-rhamnose which comprises adding a water soluble solvent to a marine alga of the family Monostromaceae, Ulvales, heating and extracting the obtained mixture to give an extract containing rhamnan sulfate; and hydrolyzing said extract followed by purification.

The marine alga of the family Monostromacease, Ulvales, as used in the process of the present invention as a raw material includes *Monostroma nitidum* Wittrock (hereinafter referred to briefly as the monostroma), *Monostroma zostericola* Tilden, *Monostroma angicava* Kjellman, *Monostroma latissimum* Wittrock and *Monostroma pulchrum* Farlow. For example, the monostroma is a green alga growing wild in the temperate regions. It is cultivated along the Pacific and the Inland Sea of Japan. An airdried product of the same has, for example, the following composition: 16.9% of moisture; 16.6% of proteins; 1.0% of lipids; 47.5% of carbohydrates; 5.6% of fibers; and 12.4% of ash. Said carbohydrates comprise polysaccharides containing approximately 60% of L-rhamnose as well as uronic acid, D-xylose, D-glucose, D-mannose and the like. The major part of the carbohydrates is present in the form of rhamnan sulfate.

The process for preparing L-rhamnose from the marine alga of the family Monostromaceae as cited above essentially comprises:

(1) extraction of rhamnan sulfate, which is a polymer of L-rhamnose, from the alga, which will be referred to as the extraction step hereinafter;

(2) hydrolysis of the extract thus obtained to form free L-rhamnose, which will be referred to as the hydrolysis step hereinafter; and (3) purification of the hydrolysate thus obtained by, for example, desalting, decoloring, concentration or crystallization, which will be referred to as the purification step hereinafter.

BEST MODES FOR CARRYING OUT THE INVENTION

Now each step as described above will be described in detail with the use of the monostroma, which can be most conveniently obtained in Japan and is the most desirable raw material for the preparation of L-rhamnose.

(1) Extraction step

We have examined various methods for the extraction of rhamnan sulfate contained in the monostroma and succeeded in an efficient extraction of the rhamnan sulfate in the following manner.

Dried monostroma is swollen and simultaneously washed by immersing in a large amount of water to thereby remove salts adhering thereto. Although it has been revealed that the subsequent procedure can be smoothly performed without removing any salt, the washing can significantly relieve the ion exchange load at the desalting step. Then the swollen alga is heated together with the water soluble solvents to thereby extract rhamnan sulfate contained in the alga. In this extraction, water soluble solvents such as water, ethylene glycol, propylene glycol, glycerol or a mixture thereof may be employed. Among these solvents, water is the most desirable since it is inexpensive and exhibits no undesirable effect on the subsequent steps.

Now the extraction step will be described in detail.

It is preferable to employ 5 to 20 parts by weight, particularly preferably 7 to 15 parts by weight, of water per part by weight of the dried monostroma. The extraction may be carried out preferably at a temperature of 90° to 160° C. The extraction period would decrease with the rise of the temperature. Namely, it is preferable to perform the extraction for 6 to 96 hours at a temperature not less than 90° C. up to 100° C., for 20 minutes to 6 hours at a temperature exceeding 100° C. up to 120° C. and for one minute to one hour at a temperature exceeding 120° C. up to 160° C. It is particularly preferable to perform the extraction for 24 to 96 hours at 100° C. or for 10 to 40 minutes at 130° C. Stirring the whole mixture would accelerate the extraction. Although the dried monostroma is employed as a raw material above, undried algae which have been just harvested may be similarly extracted as a matter of course. It is also possible to perform the extraction repeatedly with the use of a smaller amount of water in each run.

Subsequently the cells are removed by centrifugation or filtration to thereby give an extract containing rhamnan sulfate. The extract has a pH value not less than 4 in most cases. The rhamnan sulfate contained in the extract comprises a polymer of L-rhamnose having bonded sulfate groups to which are further bonded alkali metal atoms such as potassium or alkaline earth metal atoms such as magnesium. According to our analysis, this polymer contains approximately one sulfate group per molecule of L-rhamnose.

(2) Hydrolysis step

There are two methods for hydrolyzing the rhamnan sulfate contained in the extract. Although these methods are effective per se, an equally preferable result can be achieved by combining them.

The first method for the hydrolysis comprises adding acid(s) such as sulfuric, oxalic, phosphoric, hydrochloric or acetic acid or a mixture thereof in an amount of 5 to 30% by weight based on the solid content of the extract as obtained above and hydrolyzing the resulting mixture in a pressure vessel under heating. The hydrolysis may be preferably carried out at 120° to 160° C., particularly preferably at 130° to 145° C., for 0.5 to 3 hours.

The second method for the hydrolysis comprises passing the extract through a column packed with a cation exchange resin, particularly an H-type strongly acidic cation exchange resin, without adding any acid thereto, followed by heating. By passing the extract through the column packed with the cation exchange resin, cation of salts contained in the extract and those bound to the rhamnan sulfate are replaced by hydrogen ions, which lowers the pH value of the extract to approximately 1. In order to achieve a desirable result, the ion exchange resin may be preferably employed in an amount of 0.1 to 1 time by volume, still preferably 0.2 to 0.5 time by volume, based on the volume of the extract to be treated. The extract, whose pH value is thus lowered, is then hydrolyzed in a pressure vessel as such without adding any acid thereto. The hydrolysis may be carried out under the same condition as the one employed in the first method. The first and second methods may be combined to accelerate the hydrolysis. More precisely, a small amount of acid(s) may be added to the extract after treating the same with a cation exchange resin. This combined method is particularly effective when the alga to be used as the raw material are previously washed with water. This method wherein the treatment with an ion exchange resin is carried out prior to the hydrolysis is extremely effective since less anions remain in the solution from which sulfate ions are removed by, for example, calcium hydroxide in the neutralization step, which relieves the load of the ion exchange resin in the subsequent purification step.

(3) Purification step

The purification step comprises a desalting step involving desalting, decoloring and the like procedures and a crystallization step to obtain crystalized L-rhamnose.

We have examined various methods for desalting the extract hydrolyzed in the above step and have found that the following three methods are effective.

In the first desalting method, the hydrolyzate is desalted with the use of an ion exchange resin or an ion exchange membrane.

In the second desalting method, calcium or barium hydroxide or carbonate is added to the hydrolyzate and insoluble matters thus formed are removed followed by desalting with the use of an ion exchange resin.

In the third desalting method, the hydrolyzate is neutralized with an alkali and passed through an alkali metal or alkaline earth metal type of cation exchange resin to thereby separate the hydrolyzate into a portion containing sugars including L-rhamnose and another portion containing salts. Now the third method will be described in detail. After the completion of the hydrolysis, an alkali metal or alkaline earth metal hydroxide or carbonate is added to the hydrolyzate to thereby adjust the pH value thereof to 5 to 7. Then the mixture is treated with active carbon used in an amount of 1 to 5% based on the solution and filtered. A given amount of the neutralized solution thus obtained is poured onto a column packed with an alkali metal or alkaline earth metal type of cation exchange resin, preferably having the same metal as the one used in the neutralization. Then water is fed to the column. Thus an aqueous solution containing salts is eluted from the bottom of the column followed by the one containing sugars. These aqueous solutions are separately collected to give a sugar solution containing a smaller amount of salts. In order to efficiently separate the sugars from the salts, it is preferable to maintain the column at a temperature of 40° to 60° C. The sugar solutions are combined, filtered with the addition of active carbon, if required, and decolored and desalted with an ion exchange resin. This method may be performed batchwise on an industrial scale, i.e., by using a single column. Alternately it may be performed continuously, i.e., by using four to eight columns connected in series circularly; supplying the neutralized solution to the top of each column; passing water therethrough; and drawing the sugar or salt solution from the bottom of the same.

Now the crystallization step will be described. L-Rhamnose crystal may be obtained from the desalted solution generally in the following manner. The desalted solution is concentrated to a predetermined concentration, for example, in vacuo and cooled to thereby give the aimed orystals of L-rhamnose. Further an organic solvent such as ethanol may be added to the concentrated and cooled solution to thereby accelerate the crystallization of L-rhamnose, if required.

We have examined the method for further elevating the yield of the L-rhamnose obtained by the process as described above and have found that the following process gives a preferable result. Namely we have noted the fact that L-rhamnose can not be fermented by ordinary yeasts (e.g. commercially available baker's yeast is marketed at a low price) and have established a process for increasing the content of L-rhamnose in a sugar solution which comprises treating the sugar solution containing L-rhamnose with a yeast to thereby allow said yeast to ferment sugars other than L-rhamnose. As a result, the yield of the crystallized L-rhamnose can be extremely elevated, which makes the present invention further useful.

Now the process will be described in detail.

The treatment with a yeast is preferably performed during the purification step. A further preferable result may be achieved by subjecting the sugar solution from which L-rhamnose crystals are removed in the crystallization step to the yeast treatment and recovering L-rhamnose therefrom, since said sugar solutions contains a large amount of sugars which can be fermented by the yeast.

The hydrolyzate may be subjected to the yeast treatment as such, but neutralization of the same with a hydroxide or carbonate of an alkali metal or an alkaline earth metal would accerelate the fermentation. The use of calcium or barium hydroxide or carbonate as a neutralizing agent is effective in the purification following the yeast treatment since it forms insoluble salts which make the separation by filtration possible. The insoluble salts formed during the neutralization may be filtered off prior to the yeast treatment. The yeast treatment may be preferably carried out at a PH value of 3 to 8. Further the neutralized solution may be treated with active carbon and/or an ion exchange resin and then subjected to the yeast treatment. Furthermore a sugar solution obtained by the first, second or third desalting method, as described above relating to the purification step, may be subjected to the yeast treatment.

Now an embodiment of the yeast treatment will be described in detail. Baker's yeast usually in an amount of 0.5 to 5% by weight based on the solid sugars contained in the sugar solution as described above is added to the sugar solution and the mixture is stirred or allowed to stand at 25° to 45° C. for approximately 12 to 48 hours to thereby perform the fermentation of sugars other than L-rhamnose. Then the yeast cells are removed by, for example, centrifugation or filtration. Thus sugars such as D-glucose and D-mannose contained in the sugar solution are fermented into carbon dioxide gas or ethanol, which elevates the purity of L-rhamnose therein. Then the sugar solution, in which the purity of L-rhamnose is thus elevated, is purified by an appropriate desalting method selected from those as described above and concentrated. Subsequently the L-rhamnose therein is crystallized. Thus the yield of L-rhamnose is remarkably elevated compared with the case where no yeast treatment is performed.

To further illustrate the present invention, and not by way of limitation, the following Examples will be given.

EXAMPLE 1

(1) 200 g of the monostroma containing 19% of moisture and 2 l of water were introduced into a pressure vessel of approximately 5 l in volume. The mixture was gently stirred while maintaining the temperature in the vessel at 150° C. for 20 minutes followed by cooling. Then the content was taken out of the vessel and centrifuged to thereby separate the same into an aqueous solution and insoluble matters. The latter were washed with 1 l of water and the washing was combined with the aqueous solution to thereby give 2.7 kg of a solution of water-soluble components, i.e., an extract. The extract contains 122 g of solid matters which corresponds to 75.3% of the solid portion of the raw material.

(2) 10 g of conc. sulfuric acid was added to the extract as obtained in (1) and the mixture was hydrolyzed in an acid-resistant pressure vessel at 120° C. for 60 minutes.

(3) The hydrolyzate obtained in (2) was neutralized with calcium hydroxide, filtered, and then deodorized and decolored with active carbon and subjected to an ion exchanged treatment. The solution thus obtained contained sugars comprising 84% of L-rhamnose, 5% of D-glucose and 4% of D-xylose each based on the solid matters.

(4) The sugar solution obtained in (3) was concentrated in vacuo to a concentration of approximately 81% to give 21 g of crystals of L-rhamnose monohydrate. According to liquid chromatography, the purity of these crystals was 99.2%. The melting point thereof was 91.5° C. and the specific rotation of an aqueous solution thereof determined one hour after the preparation of the aqueous solution was $[\alpha]_D^{20} = +9.1°$ (in terms of anhydrous crystal).

EXAMPLE 2

(1) 200 g of the monostroma containing 20% of moisture and 1 l of water were introduced into a pressure vessel of 10 l in volume, where the mixture was extracted with steam by intermittently blowing 6 kg/cm$^2$ of steam thereto. Namely, steam was blown into the vessel for three minutes and then the extract in the vessel was collected by carefully opening a valve provided at the bottom of the vessel. After closing the valve, steam was blown again for three minutes followed by collecting the extract. This operation was repeated six times. During this operation, the temperature in the vessel was 160° C. Insoluble matters were separated by centrifugation and washed with 1 l of water. The washing was combined with the extract to thereby give approximately 5 l of an extract containing 105 g of solid matters.

(2) 26 g of conc. sulfuric acid was added to the extract obtained in (1) and the mixture was hydrolyzed in an acid-resistant pressure vessel at 130° C. for three hours.

(3) The hydrolyzate obtained in (2) was cooled and neutralized with calcium hydroxide. After filtering the calcium salts off, the filtrate was purified with the use of active carbon and an ion exchange resin. Thus a solution containing sugars comprising 81% of L-rhamnose, 4% of D-glucose and 4% of D-xylose each based on the solid matters was obtained.

(4) The sugar solution obtained in (3) was concentrated in vacuo to a concentration of approximately 83% followed by crystallization. Thus 22 g of crystals of L-rhamnose monohydrate were obtained. The purity of these crystals was 98% while the melting point thereof was 89° C.

EXAMPLE 3

(1) 500 g of the monostroma containing 17% of moisture and 1 kg of water were introduced into a pressure vessel of 10 l in volume and the mixture was heated for one hour by blowing 2.7 kg/cm$^2$ of steam thereto to give an internal temperature of 130° C. and drawing out the formed extraot every ten minutes. After cooling, the insoluble matters were separated by centrifugation and washed with warm water. The washing was combined with the extract to give approximately 6 l of the extract which had a pH value of 4.3 and contained 275 g of solid matters.

(2) 34 g of conc. sulfuric acid was added to approximately 6 l of the extract obtained in (1) and the mixture was hydrolyzed at 140° C. for 40 minutes.

(3) The hydrolyzate obtained in (2) was cooled and neutralized with calcium hydroxide. After filtering the formed calcium sulfate off, the filtrate was treated with active carbon and an ion exchange resin. Thus a solution containing sugars comprising 83% of L-rhamnose, 3% of D-glucose and 8% of D-xylose was obtained.

(4) The sugar solution obtained in (3) was concentrated in vacuo to a concentration of approximately 81% and allowed to stand overnight. Thus 54 g of L-rhamnose monohydrate was obtained in the form of white crystals. The purity of these crystals was 99% while the melting point thereof was 91° C.

EXAMPLE 4

(1) 120 g of the monostroma containing 19% of moisture and 1.2 l of water were introduced into a three-necked flask of 3 l in volume equipped with a thermometer, a condenser and a stirrer. The mixture was maintained at 100° C. therein for 24 hours with stirring. After cooling, the content was taken out of the flask and filtered to give an extract containing 80.4 g of solid matters.

(2) 29 g of conc. hydrochloric acid was added to the extract and the mixture was hydrolyzed at 130° C. for 60 minutes in an acid-resistant vessel.

(3) The hydrolyzate obtained in (2) was neutralized with 10% sodium hydroxide to give a pH value of 6. Then 20 g of active carbon was added to the solution thus neutralized and the mixture was stirred at 50° C. for one hour, filtered and concentrated to a concentration of approximately 10%. Thus 968 g of a concentrate was obtained.

(4) 300 ml of a polystyrenesulfonate cation exchange resin SK-1B (mfd. by Mitsubishi Chemical Industries, Ltd.; 50- to 100-mesh) was packed in a column (2.4 cm (int. dia.)×80 cm (height)) provided with a jacket. Then the resin was converted into a sodium type by passing diluted hydrochloric acid therethrough followed by washing with water and further passing a 5% aqueous solution of sodium chloride therethrough followed by washing with water. 60 g of the concentrate prepared in (3) was supplied from the top of this column followed by water while maintaining the column at 60° C. to thereby continuously elute the concentrate. The eluate was collected with a fraotion collector. The flow rate of the eluate was 100 ml/hr and the volume of each fraction was 12 ml. Each fraction thus collected was analyzed with liquid chromatography (column: Shimadzu SCR-101N, eluent:water). Table 1 shows the result. A solution obtained by combining the fractions No. 22 to 28 contained 92% of sugars and 8% of salts.

(5) The solution obtained by combining the fractions No. 22 to 28 as obtained in (4) was desalted by passing through 20 ml of a cation exchange resin SK-1B followed by 20 ml of an anion exchange resin WA-30 (mfd. by Mitsubishi Chemical Industries, Ltd.) and concentrated to a concentration of 70%. Then 0.9 g of ethanol corresponding to 50% by weight of the solid sugars was added thereto and the mixture was allowed to stand overnight. Thus 1.12 g of L-rhamnose monohydrate was obtained which corresponds to that 18.1 g of L-rhamnose monohydrate was obtained from 120 g of the moisture-containing monostroma. According to gas chromatography (packing liquid phase QF-1, as an acetyl derivative), the purity of L-rhamnose monohydrate was 98.8%.

TABLE 1

| Fraction No. | Salts (mg/ml) | Sugars (mg/ml) | Total (mg/ml) |
|---|---|---|---|
| 1~9 | 0 | 0 | 0 |
| 10 | 1 | 0 | 1 |
| 11 | 6 | 0 | 6 |
| 12 | 10 | 0 | 10 |
| 13 | 14 | 0 | 14 |
| 14 | 21 | 0 | 21 |
| 15 | 28 | 0 | 28 |
| 16 | 36 | 0 | 36 |
| 17 | 44 | 0 | 44 |
| 18 | 51 | 0 | 51 |
| 19 | 59 | 1 | 60 |
| 20 | 63 | 4 | 67 |
| 21 | 62 | 8 | 70 |
| 22 | 5 | 31 | 36 |
| 23 | 3 | 38 | 41 |
| 24 | 2 | 38 | 40 |
| 25 | 2 | 28 | 30 |
| 26 | 1 | 11 | 12 |
| 27 | 0 | 4 | 4 |
| 28 | 0 | 1 | 1 |
| 29 | 0 | 0 | 0 |

TABLE 2

| Fraction No. | Salts (mg/ml) | Sugars (mg/ml) | Total (mg/ml) |
|---|---|---|---|
| 1~10 | 0 | 0 | 0 |
| 11 | 1 | 0 | 1 |
| 12 | 7 | 0 | 7 |
| 13 | 16 | 0 | 16 |
| 14 | 24 | 0 | 24 |
| 15 | 31 | 0 | 31 |
| 16 | 38 | 0 | 38 |
| 17 | 43 | 0 | 43 |
| 18 | 48 | 0 | 48 |
| 19 | 51 | 0 | 51 |
| 20 | 48 | 1 | 49 |
| 21 | 42 | 3 | 45 |
| 22 | 33 | 8 | 41 |
| 23 | 18 | 21 | 39 |
| 24 | 5 | 32 | 37 |
| 25 | 2 | 31 | 33 |
| 26 | 2 | 28 | 30 |
| 27 | 1 | 20 | 21 |
| 28 | 0 | 16 | 16 |
| 29 | 0 | 6 | 6 |
| 30 | 0 | 2 | 2 |
| 31 | 0 | 0 | 0 |

EXAMPLE 5

(1) Rhamnan sulfate was extracted from the monostroma and desalted in the same manner as the one described in Example 4(1) and (2).

(2) The same column treatment as the one described in Example 4 was carried out except that the hydrolyzate obtained in (1) was neutralized with 10% potassium hydroxide and that the polystyrenesulfonate cation exchange resin was converted into a potassium type by passing a 5% aqueous solution of potassium hydroxide therethrough. Table 2 shows the result.

(3) The fractions No. 23 to 30 thus collected were combined together and subjected to the same treatment as the one described in Example 4(5). Thus 1.06 g of L-rhamnose monohydrate was obtained whioh corresponds to ihat 17.1 g of L-rhamnose monohydraie was obtained from 120 g of the moisture-containing monostroma. The purity of the same was 98.6%.

EXAMPLE 6

(1) 120 g of the monostroma containing 19% of moisture and 1.2 l of water were introduced into a three-necked flask of 3 l in volume equipped with a thermometer, a condensor and a stirrer. The mixture was maintained at 100° C. therein for 24 hours with stirring. After cooling, the content was taken out of the flask and filtered to give an extract.

(2) 20 g of 50% sulfuric acid was added to the extract obtained in (1) and the mixture was hydrolyzed in an acid-resistant vessel at 130° C. for 60 minutes. After cooling, the hydrolyzate was taken out and neutralized with calcium hydroxide to a pH value of 6. Then 20 g of active carbon was added to the neutralized mixture and the obtained mixture was stirred at 50° C. for one hour, filtered and concentrated to a concentration of approximately 10% to give 826 g of a concentrate.

(3) Then the concentrate was subjected to the same column treatment as the one described in Example 4(4) except that the polystyrenesulfonate cation exchange resin was converted into a calcium type by passing 5% calcium chloride therethrough. Table 3 shows the result.

(4) The fractions No. 25 to 34 thus collected were combined together and treated in the same manner as the one described in Example 4(5) to give 1.18 g of L-rhamnose monohydrate. This corresponds to that 16.2 g of L-rhamnose monohydrate was obtained from 120 g of the moisture-containing monostroma. The purity of the same was 98.5%.

TABLE 3

| Fraction No. | Salts (mg/ml) | Sugars (mg/ml) | Total (mg/ml) |
| --- | --- | --- | --- |
| 1~11 | 0 | 0 | 0 |
| 12 | 2 | 0 | 2 |
| 13 | 5 | 0 | 5 |
| 14 | 10 | 0 | 10 |
| 15 | 15 | 0 | 15 |
| 16 | 20 | 0 | 20 |
| 17 | 26 | 0 | 26 |
| 18 | 31 | 0 | 31 |
| 19 | 35 | 0 | 35 |
| 20 | 39 | 0 | 39 |
| 21 | 41 | 0 | 41 |
| 22 | 42 | 1 | 43 |
| 23 | 41 | 3 | 44 |
| 24 | 35 | 8 | 43 |
| 25 | 25 | 16 | 41 |
| 26 | 11 | 27 | 38 |
| 27 | 4 | 29 | 33 |
| 28 | 2 | 27 | 29 |
| 29 | 1 | 22 | 23 |
| 30 | 0 | 19 | 19 |
| 31 | 0 | 15 | 15 |
| 32 | 0 | 11 | 11 |
| 33 | 0 | 6 | 6 |
| 34 | 0 | 2 | 2 |
| 35 | 0 | 0 | 0 |

EXAMPLE 7

(1) 12 kg of the monostroma containing 19% of moisture and 140 l of water were introduced into a Stainless vessel of 300 l in volume equipped with a thermometer and a stirrer. The mixture was maintained at 96° to 100° C. therein for 72 hours with stirring. After cooling, the content was taken out of the vessel and filtered to give an extract containing 8.1 kg of solid matters.

(2) 2.9 kg of conc. hydrochloric acid was added to the extract obtained in (1) and the mixture was hydrolyzed in an acid-resistant vessel at 130° C. for 60 minutes. After cooling, the hydrolyzed mixture was taken out and neutralized with 10% sodium hydroxide to a pH value of 4. The solution thus neutralized contained 3.56 kg of sugars of the following composition:

|  | Composition (%) |
| --- | --- |
| L-rhamnose | 67.5 |
| D-glucose | 15.9 |
| D-mannose and D-galactose | 7.5 |
| D-xylose | 5.0 |
| L-arabinose | 3.3 |
| Miscellaneous | 0.8 |

(3) To the neutralized solution as obtained above, 35 g of commercially available baker's yeast was added. The yeast was allowed to ferment the sugars at 35° C. for 24 hours to give a reaction mixture which contained 2.75 kg of sugars of the following composition:

|  | Composition (%) |
| --- | --- |
| L-rhamnose | 87.3 |
| D-glucose | 0.6 |
| D-mannose and D-galactose | 0.3 |
| D-xylose | 6.5 |
| L-arabinose | 4.3 |
| Miscellaneous | 1.0 |

(4) 0.2 kg of active carbon was added to the sugar solution obtained in (3) and the obtained mixture was stirred at 50° C. for one hour, filtered, desalted with an ion exchange resin and concentrated in vacuo to a concentration of 84%. Then 1.3 kg of ethanol was added thereto to give 2.12 kg of L-rhamnose monohydrate in the form of crystals. The purity of these crystals determined by liquid chromatography was 99.2% while the melting point thereof was 91.0° C. The specific rotation of an aqueous solution thereof determined one hour after the preparation of the aqueous solution was $[\alpha]_D^{20} = +9.1°$ (in terms of anhydrous crystal).

(5) For comparison, the same procedure as described above was performed except for the step (3). Thus 1.28 kg of the crystals were obtained. The purity thereof was 98.6%.

EXAMPLE 8

(1) The procedures of Example 7(1) and (2) were followed except that the pH value of the hydrolyzate was adjusted to 6. 0.2 kg of active carbon was added to the neutralized solution and the obtained mixture was stirred at 50° C. for one hour, filtered and desalted with an ion exchange resin. Thus 300 kg of a sugar solution containing L-rhamnose at a concentration of 1% was obtained.

(2) 30 g of commercially available baker's yeast was added to the sugar solution obtained in (1) and allowed to ferment at 39° C. for 18 hours. The reaction mixture thus formed contained 2.39 kg of sugars.

(3) The sugar solution obtained in (2) was filtered through a ceramic filter to thereby remove the cells, desalted with an ion exchange resin and concentrated in vacuo to a concentration of 81%. Then 1.2 kg of ethanol was added thereto to give 1.78 kg of crystallized L-rhamnose monohydrate (purity: 99.4%). The sugar composition of each sugar solution was as follows:

|  | Example 8 (1) composition (%) | Example 8 (2) composition (%) |
| --- | --- | --- |
| L-rhamnose | 67.5 | 84.6 |
| D-glucose | 15.9 | 1.8 |
| D-mannose and D-galactose | 7.5 | 2.3 |
| D-xylose | 5.0 | 6.3 |
| L-arabinose | 3.3 | 4.0 |
| Miscellaneous | 0.8 | 1.0 |

EXAMPLE 9

(1) 300 kg of a sugar solution containing 1% of sugars, which was prepared by the same procedure as the one described in Example 8(1), was concentrated to a concentration of 84%. Then 1.7 kg of ethanol was added thereto for crystallization. The crystals thus formed were filtered to give 1.03 kg of the crystals of 98.1% in purity and 4.2 kg of a filtrate. After concentrating the filtrate and removing the ethanol therefrom, water was added thereto to give a weight of 19.7 kg. Then the concentration of this filtrate was 10%.

(2) 20 g of baker's yeast was added to the filtrate obtained in (1) and allowed to ferment the sugars at 35° C. for 24 hours. Subsequently 0.3 kg of active carbon was added thereto and the obtained mixture was filtered to remove the cells and the active carbon and desalted with an ion exchange resin.

(3) The sugar solution obtained in (2) was concentrated to a concentration of 85% and 1.7 kg of ethanol was added thereto followed by cooling and crystallizing. Thus 0.77 kg of crystals of L-rhamnose monohydrate (purity: 98.8%) was obtained.

(4) For comparison, the filtrate obtained in (1) was concentrated and crystallized as such in the same manner as the one described in (3), but no crystal of L-rhamnose monohydrate was formed.

The sugar composition of each sugar solution was as follows:

|  | Example 9 (1) composition (%) | Example 9 (2) composition (%) |
| --- | --- | --- |
| L-rhamnose | 52.9 | 77.1 |
| D-glucose | 23.1 | 1.8 |
| D-mannose and D-galactose | 11.1 | 2.3 |
| D-xylose | 7.1 | 10.3 |
| L-arabinose | 4.8 | 7.0 |
| Miscellaneous | 1.0 | 1.5 |

EXAMPLE 10

(1) 12 kg of the monostroma containing 17% of moisture and 155 l of water were introduced into a stainless vessel of 300 l in volume equipped with a thermometer, a condensor and a stirrer. The obtained mixture was maintained therein at 96° to 100° C. for 72 hours with stirring. After cooling, the supernatant of the content was filtered to give an extract of 5% in concentration. The total cation of this extract was 6,600 mg as $CaCO_3$ per liter.

(2) 145 l of the extract obtained in (1) was passed through a column (20 cm (int. dia)×1 m (height)) packed with 30 l of an H-type strongly acidic cation exchange resin SK-1B (mfd. by Mitsubishi Chemical Industries, Ltd.) followed by passing water therethrough. When 42 l of an eluate had flowed from the bottom of the column, the concentration of the eluate became constant (3.9%). The elution was further continued to thereby collect 110 l of the eluate.

(3) The eluate obtained in (2) was hydrolyzed as such at 140° C. for one hour. Thus 19.5 mg/ml of L-rhamnose was formed. After cooling, the pH value of the hydrolyzate was adjusted to 5 with 138 kg of calcium hydroxide and the insoluble calcium sulfate thus formed (4.2 kg, containing moisture) was filtered off. The total caiion of ihe filiraie was 5,600 mg as $CaCO_3$ per liier while the total anion thereof was 7,000 mg as $CaCO_3$ per liter.

(4) For comparison, the above procedure except the step (2) was followed and conc. sulfuric acid containing 12.5% of solid matters was added to the mixture thus obtained. The resulting mixture was hydrolyzed at 140° C. for one hour. Thus L-rhamnose was formed in an amount (19.7 mg/ml) comparable to that of (3). Similarly to the procedure of (3), the mixture was cooled and neutralized to a pH value of 5 with 0.94 kg of calcium hydroxide. Then calcium sulfate thus formed (2.3 kg, containing moisture) was filtered off. The total cation of the filtrate was 12,800 mg as $CaCO_3$ per liter while the total anion thereof was 13,000 ml as $CaCO_3$ per liter.

(5) 28 g of active carbon was added to the sugar solution as obtained in (3) and the mixture was stirred at 50° C. for one hour, filtered, desalted with an ion exchange resin and concentrated in vacuo to a concentration of 80%. Then 1.4 kg of ethanol was added thereto for crystallization. Thus 1.22 kg of crystals of L-rhmnose monohydrate were obtained. The purity of these crystals determined with liquid chromatography was 98.8% while the melting point thereof was 89.5° C. The specific rotation of an aqueous solution thereof determined one hour after preparing the aqueous solution was $[\alpha]_D^{20} = +9.1°$ (in terms of anhydrous crystal).

EXAMPLE 11

(1) 12 kg of the monostroma containing 17% of moisture was washed with 500 l of water to thereby remove salts adhering to the alga. Thus a trace amount of rhamnan sulfate and 2.26 kg of various salts were washed away. After the washing, 132 kg of the alga containing moisture was introduced into a stainless vessel of 300 l in volume and maintained therein at 96° to 100° C. for 48 hours with stirring. After cooling, the content was filtered to give an extract of 4% in concentration. The total cation of the extract was 2,100 mg as $CaCO_3$ per liter.

(2) 85 l of the extract obtained in (1) was passed through a column (15 cm (int. dia.)×1.2 m (height)) packed with 20 l of an H-type strongly acidic cation exchange resin SK-1B (mfd. by Mitsubishi Chemical Industries, Ltd.) followed by passing water therethrough. When 10 l of an eluate has flowed from the bottom of the column, the concentration of the eluate became constant (3.2%). Then the elution was further continued to thereby collect 60 l of the eluate.

(3) The eluate obtained in (2) was hydrolyzed as such at 140° C. for one hour. Thus 20.5 mg/ml of L-rhamnose was formed. After cooling, the hydrolydate was neutralized with 0.82 kg of calcium hydroxide to a pH value of 5.8. The insoluble calcium sulfate thus formed (3.15 kg, containing moisture) was filtered off. The total cation of the filtrate was 2,800 mg as $CaCO_3$ per liter while the total anion thereof was 2,900 mg as $CaCO_3$ per liter.

(4) 24 g of active carbon was added to the sugar solution obtained in (3) and the mixture was stirred at 50° C. for one hour, filtered, desalted with an ion exchange resin and concentrated in vacuo to a concentration of 80%. Then 1 kg of ethanol was added thereto for crystallization. Thus 1.03 kg of crystals of L-rhamnose monohydrate were obtained. The purity of these crystals determined with liquid chromatography was 98.8% while the melting point thereof was 89.5° C. The specific rotation of an aqueous solution thereof determined one hour after the preparation of the aqueous solution was $[\alpha]_D^{20} = +9.1°$ (in terms of anhydrous crystal).

We claim:

1. Process for preparing L-rhamnose, which comprises extracting a marine alga belonging to the family Monostromaceae, Ulvales, with a watersoluble solvent under heating at a temperature of 90° to 160° to provide an extract containing rhamnan sulfate and attendant impurity constituents also extracted with the rhamnan sulfate from said alga, thereafter hydrolyzing said extract by adding acid to form a hydrolysate containing free L-rhamnose and recovering the L-rhamnose in purified form from said hydrolysate.

2. Process of claim 1 wherein said marine alga is *Monostroma nitidum* Wittrock.

3. Process of claim 1 wherein said solvent is water.

4. Process of claim 1 wherein said acid is selected from the group consisting of sulfuric, oxalic, phosphoric, hydrochloric and acetic acid, an mixtures thereof.

5. Process of claim 1, wherein said extracting is carried out at a temperature of $\geq 90°$ C. to $\leq 100°$ C. for a time period of 6 to 96 hours.

6. Process of claim 1, wherein said extracting is carried out at a temperature of $>100°$ C. to $\leq 120°$ C. for a time period of 20 minutes to 6 hours.

7. Process of claim 1, wherein said extracting is carried out at a temperature of $>120°$ to $\leq 160°$ C. for a time period of 1 minute to 1 hour.

8. Process for preparing L-rhamnose, which comprises extracting a marine alga belonging to the family Monostromaceae, Ulvales, with a water soluble solvent under heating at a temperature of 90° to 160° C. to provide an extract containing rhamnan sulfate and attendant impurity constituents comprising proteins, lipids, fibers, ash, uronic acid, D-xylose D-glucose and D-mannose and thereafter hydrolyzing said extract to form a hydrolysate containing free L-rhamnose, said hydrolzing being effected by a hydrolyzing step selected from the group consisting of (a) adding acid to the extract,
(b) passing the extract through a column packed with a cation exchange resin and
(c) passing the extract through a column packed with a cation exchange resin and adding acid thereto and recovering the L-rhamnose in purified form from the hydrolysate by removing said attendant impurity constituents from the hysrolysate and isolating the L-rhamnose from the resulting hydrolysate, after said removing of said attendant impurity constituents, by crystallization.

9. Process of claim 8 wherein said removing is effected by desalting the hydrolysate with an ion exchange resin or ion exchange membrane.

10. Process of claim 8 wherein said removing is effected by adding a hydroxide or carbonate of calcium or barium to the hydrolysate, removing insoluble salts thus formed and thereafter treating the resultant hydrolysate with an ion exchange resin.

11. Process of claim 8 wherein said removing is effected by neutralizing the hydrolysate with an alkali and then treating the neutralized hydrolysate with an alkali metal or alkaline earth metal cation exchange resin.

12. Process of claim 9, 10 or 11 wherein said removing is further effected by a procedure comprising adding a yeast to the hydrolysate thereby to allow said yeast to ferment sugars other than L-rhamnose and then removing the yeast by centrifugation or filtration.

13. Process of claim 8 wherein said marine alga is *Monostroma nitidum* Wittrock.

14. Process of claim 8 wherein said solvent is water.

15. Process of claim 8 wherein the acid of said step (a) and said step (c) is selected from the group consisting of sulfuric, oxalic, phosphoric, hydrochloric and acetic acid, and mixtures thereof.

16. Process of claim 8, wherein said extracting is carried out at a temperature of $\geq 90°$ C. to $\leq 100°$ C. for a time period of 6 to 96 hours.

17. Process of claim 8, wherein said extracting is carried out at a temperature of $>100°$ C. to $\leq 120°$ C. for a time period of 20 minutes to 6 hours.

18. Process of claim 8, wherein said extracting is carried out at a temperature of $>120°$ C. to $\leq 160°$ C. for a time period of 1 minute to 1 hour.

* * * * *